Sept. 20, 1949. R. N. SHIRAS ET AL Re. 23,151
ISOMERIZATION OF CYCLOPARAFFINS OF NONHYDROAROMATIC STRUCTURE
Original Filed Oct. 18, 1946
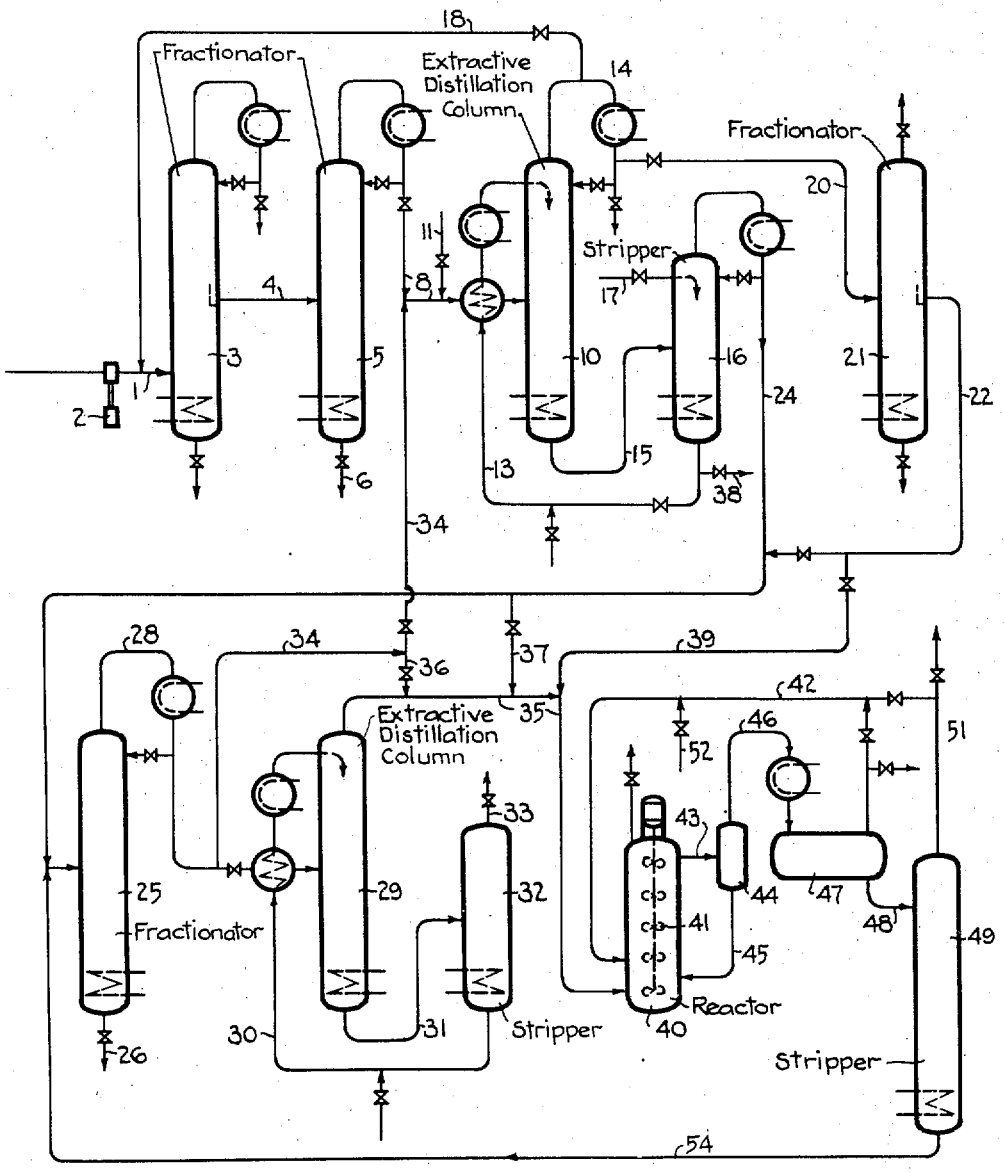
Inventors: Russell N. Shiras
Alan C. Nixon
Carl H. Deal, Jr.
By their Agent: E. Walter Mack Reissued Sept. 20, 1949

Re. 23,151

UNITED STATES PATENT OFFICE 23,151

ISOMERIZATION OF CYCLOPARAFFINS OF NONHYDROAROMATIC STRUCTURE

Russell N. Shiras, Oakland, Alan C. Nixon, Berkeley, and Carl H. Deal, Jr., Alameda, Calif., assignors to Shell Development Company, San Francisco, Calif., a corporation of Delaware Original No. 2,460,852, dated February 8, 1949, Serial No. 703,992, October 18, 1946. Application for reissue July 16, 1949, Serial No. 105,242

8 Claims. (Cl. 260—666)

This invention relates to the production of cycloparaffins of hydroaromatic structure from hydrocarbon mixtures of relatively wide boiling range such as naphthenic gasolines or fractions thereof comprising cycloparaffins of hydroaromatic structure and non-hydroaromatic structure in admixture with open chain paraffin and aromatic hydrocarbons. The invention relates more particularly to an improved process for the more efficient production of cyclohexane from naphthenic gasolines and fractions thereof comprising methylcyclopentane and cyclohexane.

Realization of the full advantages inherent in processes relying upon cycloparaffins of hydroaromatic structure, such as, for example, cyclohexane, as a starting or intermediate material is often dependent upon efficient practical scale production of such cycloparaffins from the available complex hydrocarbon mixtures comprising them. Not only is it imperative that they be produced with high yields, but it is essential that the product obtained be of a relatively high purity and yet involve the use of a minimum of operative steps in their production.

Sources of cycloparaffins of hydroaromatic structure include the available hydrocarbon mixtures such as, for example, the naphthenic, natural and straight run gasolines, etc. Other sources include hydrocarbon mixtures of naphthenic character, boiling in the gasoline boiling range obtained by fractionation of the products of the process involving the thermal or catalytic treatment of hydrocarbons or carbonaceous materials. Efficient production of a cycloparaffin of hydroaromatic structure such as, for example, cyclohexane from such readily available hydrocarbon mixtures of naphthenic character involves not only the problem of recovering at least a substantial part of the cyclohexane inherently present in such mixtures, but the simultaneous conversion of the cycloparaffins of non-hydroaromatic structure to cycloparaffins of hydroaromatic structure, such as the conversion of the initially present methylcyclopentane to cyclohexane. The readily available naphthenic hydrocarbon mixtures as is well known, however, consist of highly complex mixtures of a plurality of individual hydrocarbons, many of which have similar or closely approximating boiling temperatures, and many of which are capable of forming azeotropes with one another during the conditions of fractional distillation.

Separation of cycloparaffins free of any substantial amount of impurities from such complex mixtures by such methods of fractional distillation disclosed heretofore, if at all possible, is often rendered so involved and delicate an operation as to render it highly impractical. Resort to such expedients as the initial separation of a fraction comprising both methylcyclopentane and cyclohexane, subjection of this fraction to cycloparaffin isomerizing conditions, and fractionation of the isomerizate by methods disclosed in processes heretofore is therefore unsatisfactory. Not only do they enable the attainment of only relatively low conversions of cycloparaffins of non-hydroaromatic structure to cycloparaffins of hydroaromatic structure but the product thereby obtained will generally comprise substantial amounts of contaminant materials such as aromatic hydrocarbons and open chain paraffins, the boiling temperatures of which lie so close to those of the desired cycloparaffins as to render their separation therefrom by such expedients as simple fractionation by methods disclosed heretofore impractical. In the production of cyclohexane from readily available naphthenic hydrocarbon mixtures by such methods, the cycloparaffins produced will be contaminated with substantial amounts of the benzene and dimethylpentanes originally present in the charge. A serious difficulty generally inherent in processes disclosed heretofore wherein benzene is unavoidably accumulated in the isomerizate is the highly disadvantageous limitation upon the amount of unconverted material which can be recycled. For the removal of sufficient benzene to avoid an inordinate accumulation in the system requires the rejection therewith of at least a substantial part of the unconverted material constituting the recycle stream in such methods. Since the suitability of a cyclohexane as starting or intermediate material in many processes is dependent upon the absence therein to any substantial degree of benzene and dimethylpentanes, it is apparent that the practicability of a process producing cyclohexane from readily available complex naphthenic hydrocarbon mixtures relies upon the ability of the process to produce cyclohexane efficiently and free of any substantial amount of benzene and dimethylpentane. By the term "hydroaromatic cycloparaffins," as used throughout the specification and appended claims is meant the cycloparaffins having a hexamethylene ring such as, for example, cyclohexane, and the alkyl cyclohexanes, to distinguish them from cycloparaffins of non-hydroaromatic structure comprising those having pentamethylene rings such as, for example, methylcyclopentane and other cyclopentanes.

It is an object of the present invention to provide an improved process for the more efficient production of cycloparaffins of hydroaromatic structure from hydrocarbon mixtures of relatively wide boiling range such as naphthenic gasolines, or fractions thereof, comprising cycloparaffins of hydroaromatic and non-hydroaromatic structure in admixture with close boiling aromatic and open chain paraffinic hydrocarbons.

Another object of the invention is the provision of an improved process for the more efficient production of cyclohexane from hydrocarbon mixtures of relatively wide boiling range such as naphthenic gasolines.

A more particular object of the invention is the provision of an improved process for the more efficient production of cyclohexane of a high degree of purity from naphthenic gasoline fractions comprising methylcyclopentane, cyclohexane, benzene and close boiling open chain paraffinic hydrocarbons.

In accordance with the process of the invention a hydrocarbon mixture of naphthenic character such as for example a naphthenic straight run gasoline is subjected to fractionation to separate therefrom a fraction predominating in hydrocarbons having the same number of carbon atoms to the molecule and comprising cycloparaffins of non-hydroaromatic structure and cycloparaffins of hydroaromatic structure in admixture with close boiling aromatic and open chain paraffins. The cycloparaffin-containing fraction thus obtained is subjected to extractive distillation conditions in the presence of a suitable solvent as described more fully below to separate therefrom cycloparaffins of hydroaromatic and non-hydroaromatic structure free of any substantial amounts of close boiling contaminants comprising open chain paraffins and aromatic hydrocarbons. The cycloparaffins of non-hydroaromatic structure free of any substantial amount of aromatic and open chain paraffins thus obtained are subjected to cycloparaffin isomerizing conditions converting cycloparaffins of non-hydroaromatic structure to cycloparaffins of hydroaromatic structure.

In a preferred embodiment of the invention the cycloparaffin-containing fraction separated from the naphthenic gasoline and including cycloparaffins of hydroaromatic and non-hydroaromatic structure in admixture with close boiling contaminants comprising open chain paraffins and aromatic hydrocarbons, is subjected to an extractive distillation in a first extractive distillation zone. In the first extractive distillation zone a raffinate fraction comprising paraffinic hydrocarbons is separated from an extract fraction comprising cycloparaffins of hydroaromatic and non-hydroaromatic structure in admixture with aromatic hydrocarbons having the same number of carbon atoms to the molecule as the cycloparaffins. The extract fraction from the first extractive distillation zone is passed into a cycloparaffin separating zone wherein a vapor fraction comprising cycloparaffins of non-hydroaromatic structure and aromatic hydrocarbons is separated from a liquid fraction comprising cycloparaffins of hydroaromatic structure free of any substantial amount of aromatics. The vapor overhead from the cycloparaffin separating zone is passed into a second extractive distillation zone. In the second extractive distillation zone a raffinate comprising cycloparaffins of non-hydroaromatic structure free of any substantial amount of aromatics is separated from an extact fraction comprising aromatic hydrocarbons. The raffinate comprising cycloparaffins of non-hydroaromatic structure free of any substantial amount of aromatics is introduced into a cycloparaffin conversion zone. In the conversion zone the cycloparaffins are subjected to catalytic cycloparaffin isomerizing conditions effecting the conversion of cycloparaffins of non-hydroaromatic structure to cycloparaffins of hydroaromatic structure having the same number of carbon atoms to the molecule. Effluence from the conversion zone comprising cycloparaffins of hydroaromatic and non-hydroaromatic structure is introduced into the cycloparaffin separating zone. As will become apparent from the following description thereof, the invention enables not only the recovery of at least a substantial part of all of the cycloparaffin content of a cycloparaffin concentrate as cycloparaffins of hydroaromatic structure, but results in the obtaining of a product of a high degree of purity, devoid of even such contaminants as aromatics of close boiling range, with a minimum of steps and in the absence of many of the difficulties and complexities inherent in attempts to obtain a cycloparaffin product of a similar degree of purity by methods available heretofore.

In order to set forth more fully the nature of the invention, it will be described in detail in its application to the production of cyclohexane of a high degree of purity, free of any substantial amounts of benzene, from hydrocarbon mixtures of naphthenic character in the gasoline boiling range, with reference to the attached drawing in which the single figure represents a more or less diagrammatic elevational view of a form of apparatus suitable for executing the process of the invention.

A hydrocarbon mixture of naphthenic character such as, for example, a naphthenic straight run gasoline, is forced from an outside source through valved line 1 by means of pump 2 into a feed fractionating zone comprising fractionator 3. Within fractionator 3 a hexane fraction comprising methylcyclopentane and cyclohexane is separated as an intermediate fraction. The methylcyclopentane - cyclohexane fraction is passed from fractionator 3 through line 4 into a second feed fractionator 5. Fractionation within fractionator 3 is preferably controlled to concentrate substantially all of the six carbon atom cycloparaffins originally present in the feed in the intermediate methylcyclopentane-cyclohexane fraction. Although the boiling range of the fraction thus obtained may vary within the scope of the invention, depending upon the particular origin of the composition of the feed material, a hexane fraction boiling in the range of, for example, from about 65° C. to about 85° C. has been found suitable. Within fractionator 5 the hexane fraction is subjected to a second fractionation to effect the separation of a higher boiling fraction as bottoms from a vapor overhead fraction comprising cyclohexane and methylcyclopentane. Operating conditions within fractionator 5 may be controlled to include at least a substantial part of the dimethylpentanes originally present in the feed in the liquid bottoms. Bottoms from fractionator 5 are withdrawn therefrom through valved line 6 and may be sent to additional cycloparaffin separating means, not shown in the drawing, to effect the recovery of any cyclohexane contained therein.

The vapor fraction is taken overhead from fractionator 5 and passed through valved line 8 into a first extractive distillation zone. A fraction comprising methylcyclopentane and cyclohexane from any suitable outside source may be introduced into the system by means of valved line 11. Such a fraction may constitute a part of or all of the hydrocarbon charge to the system. The overhead fraction from tower fractionator 5 will comprise besides methylcyclopentane and cyclohexane a certain amount of open chain paraffins and at least a substantial part of the benzene originally present in the charge. The first extractive distillation zone may comprise an extractive distillation column 10. Within column 10 the cycloparaffin concentrate is subjected to an extractive distillation in the presence of a suitable solvent introduced into the upper part of the column from a suitable source by means of line 13.

Solvents which may be employed in column 10 include any solvent material enabling the separation of open chain paraffins as a vapor fraction from a liquid fraction comprising the solvent and the cycloparaffins under extractive distillation conditions. Suitable solvents comprise solvents for hydrocarbons which are higher boiling than the cycloparaffins being distilled, are stable under the conditions of distillation, do not react with any of the components of the hydrocarbon feed, and which markedly increase the volatility of the open chain paraffins relative to those of the cycloparaffins. Suitable solvents comprise, for example, the polar liquids such as for example any of the polar solvents for cycloparaffins higher boiling than cyclohexane having oxygen-, nitrogen-, or sulfur-containing polar groups such as for example phenol, benzoic acid, isobutyric acid, aniline, N-methylaniline, cyclohexylamine, N-cyclohexylaniline, diphenylamine, napthylamine, hexamethylamine diamine, benzaldehyde, furfuraldehyde, zenzoic anhydride, ethylbenzoate, benzophenone, acetophenone, cyclohexanone; benzoin, benzonitrile, nitrobenzene, nitropropane, pentachloroethane, diphenyl ether, acetal, acetamide, ethylphosphate, dimethylsulfolane, the alkyl-substituted sulfolanes, etc. The solvent employed may consist of a single compound or of solutions of two or more of such compounds or of aqueous solutions thereof.

Extractive distillation conditions within column 10 are controlled to effect the separation of a vapor raffinate comprising open chain paraffins from a liquid extract comprising the solvent, methylcyclopentane and cyclohexane. The benzene present in the charge to column 10 will be included, under extractive distillation conditions effecting the separation of paraffins from cycloparaffins in the cycloparaffin extract.

The vapor raffinate fraction is taken overhead from column 10 by means of valved line 14. The liquid extract fraction is taken from the lower part of column 10 and passed through line 15 into a stripping zone comprising still 16 wherein the cycloparaffins comprising methylcyclopentane and cyclohexane in admixture with benzene are separated as a vapor fraction from a liquid fraction comprising the solvent. Lean solvent is returned from still 16 to the upper part of column 10 by means of valved line 13.

The process of the invention enables substantially complete recovery of the six carbon atom cycloparaffins originally present in the feed. In a preferred method of effecting such substantially complete recovery of all the six carbon atom cycloparaffins in the feed, conditions in fractionator 5 are controlled so that substantially all of the cyclohexane in the charge thereto is taken overhead. This will generally result in the inclusion of a proportion of the dimethylpentanes in the overhead. Dimethylpentanes thus included in the overhead of fractionator 5 are separated therefrom to the degree desired in column 10 of the first extractive distillation zone. Inclusion of substantially all of such dimethylpentanes in the paraffinic overhead of column 10 will occasion the entrainment therewith of a certain amount of the methylcyclopentane. When methylcyclopentaen is thus included to a substantial degree in the overhead from column 10 it is perferably recovered therefrom by recycling at least a part of the overhead stream from line 14 through valved line 18 to line 1 leading into fractionator 3. The overhead from column 10 may be passed, in part or in its entirety, through valved line 20, to a separate fractionating zone represented in the drawing by the single fractionator 21. Within fractionator 21 a fraction comprising lighter boiling materials, such as open chain hexanes, is separated from a liquid higher boiling fraction comprising dimethylpentanes. Since the lower boiling of the six carbon atom cycloparaffins is readily separated by fractionation from dimethylpentane, an intermediate fraction comprising methylcyclopentane free of any substantial amount of dimethylpentane is separated in fractionator 21 and removed therefrom by means of line 22.

Overhead from stripper 16 comprising methylcyclopentane, cyclohexane and benzene, free of any substantial amount of dimethylpentanes, is passed through line 24 into a cycloparaffin separating zone. When operating the process with the passage of overhead from column 10 to fractionator 21, the methylcyclopentane withdrawn from fractionator 21 through line 22, is passed in part or entirety into line 24 to combine therein with the cycloparaffin overhead from stripper 16.

The cycloparaffin separating zone may comprise a fractionator 25. In fractionator 25 a fraction comprising cyclohexane is separated from a vapor fraction comprising methylcyclopentane and benzene. The liquid fraction comprising cyclohexane is withdrawn from fractionator 25 by means of valved line 26 and eliminated from the system as a final product. The vapor fraction comprising methylcyclopentane and benzene is withdrawn overhead from fractionator 25 and passed through valved line 28 into a second extractive distillation zone. The second extractive distillation zone may comprise an extractive distillation column 29. Within column 29 the hydrocarbon stream is distilled in the presence of a suitable solvent which is introduced into the upper part of the column by means of line 30. Extractive distillation conditions are controlled within column 30 to effect the separation of a raffinate vapor overhead comprising methylcyclopentane free of any substantial amount of benzene from a liquid extract fraction comprising solvent and benzene. Suitable solvents for use in column 29 comprise those set forth for the separation of cycloparaffins from open chain paraffins in column 10. Thus good results are attained by the use of phenol or any other polar solvent for benzene which is higher boiling than benzene and stable under the operating conditions, to effect the indicated separation of methylcyclopentane from benzene.

The vapor fraction comprising methylcyclopentane free of any substantial amount of benzene is passed from column 29 through line 35 to a conversion zone.

The liquid fraction comprising benzene and solvent is passed from extractive distillation column 29 through line 31 into a stripper 32. Within stripper 32 benzene is stripped from the solvent and eliminated as overhead therefrom through line 33. Lean solvent is withdrawn from stripper 16 and passed through line 30 to column 29.

It is thus seen that the process of the invention enables not only the substantially complete recovery of cyclohexane free of any substantial amount of benzene from the charge, but provides for the separation of a methylcyclopentane charge for the conversion zone which is also free of any substantial amount of benzene. Modification may obviously be made within the scope of the invention without departing from the spirit and scope thereof. Thus if desired the cycloparaffin-rich solvent withdrawn from column 10 may be stripped of only the methylcyclopentane in stripper 16. Additional solvent may then be introduced from an outside source by means of valved line 17. The substantially pure methylcyclopentane thus obtained overhead from stripper 16 may be passed directly to the conversion zone. To this effect a valved line 37 is provided enabling the passage of hydrocarbons from line 24 into line 35 leading to the conversion zone. When thus taking only methylcyclopentane overhead in stripper 16, the solvent now still containing cyclohexane as well as benzene is drawn therefrom through line 13 and by-passed through a valved line 38 to suitable cyclohexane and benzene recovery means not shown in the drawing. Such recovery means may comprise one or more separate stripping zones as well as one or more separate solvent extraction or extractive distillation zones. When the benzene is thus diverted from the system through line 38 and no benzene is sent to the cycloparaffin separating column 25, the benzene-free overhead from column 25 may be passed directly to the conversion zone by means of valved lines 28, 34, 36 and 35.

When methylcyclopentane is passed from fractionator 21 through valved line 22, such methylcyclopentane stream may also be introduced directly into the conversion zone. To this effect a valved line 39 is provided to enable the passage of methylcyclopentane from line 22 into line 35. An outstanding feature of the process of the invention is the efficient separation of benzene from cyclohexane. The separation of benzene from cyclohexane is greatly aided in column 25 by the presence therein of substantial amounts of methylcyclopentane which is taken overhead with the benzene. The passage of methylcyclopentane, even though free of benzene, from line 22, through line 24, into fractionator 25, may be resorted to to obtain the additional advantage of its presence upon the efficient separation of benzene from cyclohexane.

The conversion zone may comprise one or more reaction vessels such as for example, a reactor 40, provided with suitable stirring means 41. Within reactor 40 the methylcyclopentane is contacted with an isomerization catalyst under cycloparaffin isomerizing conditions. Suitable catalysts comprise those containing a metal halide of the Friedel-Crafts type, particularly those comprising a halide of aluminum, such as $AlCl_3$ and/or $AlBr_3$. Particularly suitable catalysts comprise the organo-aluminum halide complexes, preferably a preformed aluminum chloride hydrocarbon complex. Other suitable catalysts comprise those of the molten salt type containing the aluminum chloride in admixture with one or more halide salts. The temperature in the conversion zone 40 is maintained in the range of from about 20° C. to about 150° C. and preferably from about 50° C. to about 95° C. The specific temperature employed will be dependent to some extent upon the particular catalyst employed. When utilizing a preformed aluminum chloride hydrocarbon complex as the catalyst a temperature in the range of from about 65° C. to about 85° C. is somewhat preferred. A hydrogen halide promoter, such as for example hydrogen chloride, is preferably introduced into reactor 40 by means of line 42. The hydrogen chloride may be introduced in an amount of, for example, from about 0.1% to about 5% and preferably in an amount below about 1%. A greater or lesser amount of hydrogen halide may, however, be introduced into the reaction zone within the scope of the invention. Under these conditions methylcyclopentane is converted to cyclohexane within reactor 40.

Effluence from reactor 40 comprising cyclohexane, and unconverted methylcyclohexane, entrained catalyst and hydrogen halide, is passed through line 43 into a catalyst separating zone, such as a separator 44. Within separator 44 a catalyst layer is separated from a supernatant hydrocarbon layer. Catalyst is passed from separator 44 through line 45 to reactor 40. The hydrocarbon layer is passed from separator 44, through line 46, into an accumulator 47. Liquid comprising cycloparaffins and dissolved hydrogen chloride is passed from accumulator 47 through line 48 into a stripping tower 49. Within stripper 49 there is separated a vapor overhead comprising hydrogen halide which is recycled through valved lines 51 and 42 to the conversion zone. A valved line 52 is provided for the introduction of makeup hydrogen chloride into the system.

A liquid fraction comprising cyclohexane and unconverted methylcyclopentane is taken from the lower part of stripper 49 and passed through line 54 into fractionator 25. To aid in avoiding the accumulation of light materials within the system without loss of valuable cycloparaffins, a part of the overhead from fractionator 25 may be passed intermittently or continuously from line 28, through line 34, into line 8 leading to the first extractive distillation column 10.

A further signal advantage of the process of the invention resides in the ability to employ a total recycle from the isomerization zone therein. Due to the substantially complete elimination of benzene from the reactor charge without loss of any substantial amount of cycloparaffins from the system, all of the methylcyclopentane content of the reactor effluence is returned to the reaction zone, thereby attaining substantially complete conversion to cyclohexane of all methylcyclopentane charged to the process and its recovery as a benzene-free product. The invention therefore eliminates the difficulties often inherent in processes disclosed heretofore, wherein at least a substantial portion of the cycloparaffin-containing recycle stream must be sacrificed to effect the elimination of sufficient benzene to prevent its accumulation within the system.

The following example is illustrative of the practical scale production of high purity, benzene-free cyclohexane from a naphthenic straight run gasoline in accordance with the process of the invention:

*Example*

In a continuous plant scale operation 8200 barrels of straight run naphthenic gasoline containing 7.1% of methylcyclopentane, 2.73% of cyclohexane and 0.83% of benzene by volume, are subjected to a first fractional distillation to separate therefrom a hexane fraction boiling in the range of from about 65° C. to about 85° C. The resulting hexane fraction is subjected to a second fractionation to separate therefrom a $C_6$ cycloparaffin concentrate boiling in the range of from about 65° C. to about 78° C. containing 41.14% methylcyclopentane, 11.10% cyclohexane, 4.5% benzene and 2.28% dimethylpentanes, the remainder of the concentrate consisting essentially of lower boiling and higher boiling paraffins.

The $C_6$ cycloparaffin concentrate thus obtained is subjected to a first extracted distillation in the presence of phenol as the solvent to separate an overhead raffinate consisting essentially of paraffins from a liquid bottoms extract consisting essentially of solvent, cycloparaffin and aromatics. The rich extract-containing solvent is stripped to obtain an extract fraction consisting essentially of methylcyclopentane, cyclohexane and benzene, substantially free of paraffins, which is passed into a cycloparaffin fractionator into which the hydrocarbon effluent from the subsequent reaction zone is also introduced. In the cycloparaffin fractionator a vapor overhead containing methylcyclopentane and aromatics is separated from a liquid bottoms fraction consisting essentially of benzene-free cyclohexane. The overhead from the cycloparaffin fractionator contains 7.5% normal hexane, 84.07% methylcyclopentane, 0.9% cyclohexane and 6.07% benzene. The overhead from the cycloparaffin fractionator is subjected to a second extractive distillation in the presence of phenol as the solvent resulting in the obtaining of a substantially benzene-free raffinate containing 8% normal hexane, 89.4% methylcyclopentane and 1% cyclohexane. Benzene is stripped from the rich phenol solvent and recovered as 99.8% pure benzene. The benzene-free raffinate from the second extractive distillation zone is subjected to cycloparaffin isomerizing conditions by contact with an aluminum chloride-hydrocarbon complex at a temperature of 80° C. and in the presence of a 0.4% HCl. The hydrocarbon components of the reactor effluent containing 40.7% methylcyclopentane and 48.7% of cyclohexane are passed directly into the cycloparaffin fractionator. Benzene-free liquid bottoms having a 91.5% by volume content of cyclohexane is drawn as the bottoms fraction from the cycloparaffin fractionator. Redistillation of this cyclohexane fraction results in a benzene-free cyclohexane of 95% purity. 87% of the combined methylcyclopentane and cyclohexane originally present in the gasoline charge to the system is thus recovered as benzene-free cyclohexane of 95% purity.

For the purpose of clarity, parts of apparatus such as pumps, coolers, reboilers, condensers, valves, etc., not essential to a complete understanding of the invention have been omitted from the drawing. Fractionating zones depicted in the drawing by single fractionators may comprise the use of more than one fractionator in the execution of the invention on a practical scale.

The invention claimed is:

1. The process for the production of cyclohexane free of any substantial amount of benzene from naphthenic gasoline which comprises separating a fraction comprising methylcyclopentane and cyclohexane in admixture with close boiling open chain paraffins and benzene from said gasoline, subjecting said fraction to extractive distillation in a first extractive distillation zone, separating a raffinate fraction comprising paraffins from an extract fraction comprising methylcyclopentane, cyclohexane and benzene in said first extractive distillation zone, passing said extract fraction from said first extractive distillation zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone with an isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

2. The process for the production of cyclohexane free of any substantial amount of benzene from naphthenic gasoline which comprises separating a fraction comprising methylcyclopentane and cyclohexane in admixture with close boiling open chain paraffins and benzene from said gasoline, subjecting said fraction to extractive distillation in a first extractive distillation zone, separating a raffinate fraction comprising paraffins from an extract fraction comprising methylcyclopentane, cyclohexane and benzene in said first extractive distillation zone, passing said extract fraction from said first extractive distillation zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone with an aluminum chloride isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

3. The process for the production of cycloparaffins of hydroaromatic structure free of any substantial amount of aromatic hydrocarbons from a naphthenic gasoline which comprises separating a fraction comprising cycloparaffins of hydroaromatic and non-hydroaromatic structure in admixture with close boiling open chain paraffin and aromatic hydrocarbons from said gasoline, subjecting said fraction to extractive distillation in a first extractive distillation zone, separating a raffinate fraction comprising paraffins from an extract fraction comprising cycloparaffins of hydroaromatic and non-hydroaromatic structure in admixture with close boiling aromatic hydrocarbons in said first extractive distillation zone, passing said extract fraction from said first extractive distillation zone into a cycloparaffin fractionating zone, separating a vapor fraction comprising cycloparaffins of non-hydroaromatic structure and close boiling aromatic hydrocarbons from a liquid fraction consisting essentially of cycloparaffins of hydroaromatic structure free of any substantial amount of aromatic hydrocarbons in said cycloparaffin fractionating zone, passing said vapor fraction from said cycloparaffin fractionating zone into a second extractive distillation zone, separating a raffinate fraction comprising cycloparaffins of non-hydroaromatic structure free of any substantial amount of aromatic hydrocarbons from an extract fraction comprising aromatic hydrocarbons in said second extractive distillation zone, contacting said raffinate fraction from said second extractive distillation zone with an isomerization catalyst at cycloparaffin isomerizing conditions in a conversion zone, thereby converting cycloparaffins of non-hydroaromatic structure to cycloparaffins of hydroaromatic structure in said conversion zone, passing effluence from said conversion zone into said cycloparaffin fractionating zone, and withdrawing said liquid fraction consisting essentially of cycloparaffins of hydroaromatic structure free of any substantial amount of aromatic hydrocarbons from said cycloparaffin fractionating zone.

4. The process for the production of cyclohexane free of any substantial amount of benzene from a hydrocarbon fraction comprising methylcyclopentane and cyclohexane in admixture with close boiling open chain paraffins and benzene, which comprises subjecting said fraction to extractive distillation in a first extractive distillation zone, separating a raffinate fraction comprising paraffins from an extract fraction comprising methylcyclopentane, cyclohexane and benzene in said first extractive distillation zone, passing said extract fraction from said first extractive distillation zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone with an isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

5. The process for the production of cyclohexane free of any substantial amount of benzene from a hydrocarbon fraction comprising methylcyclopentane and cyclohexane in admixture with close boiling open chain paraffins and benzene, which comprises subjecting said fraction to extractive distillation in a first extractive distillation zone, separating a raffinate fraction comprising paraffins from an extract fraction comprising methylcyclopentane, cyclohexane and benzene in said first extractive distillation zone, passing said extract fraction from said first extractive distillation zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone with an aluminum halide isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

6. The process for the production of cycloparaffins of hydroaromatic structure free of any substantial amount of aromatic hydrocarbons from a hydrocarbon fraction comprising cycloparaffins of hydroaromatic and non-hydroaromatic structure in admixture with close boiling open chain paraffin and aromatic hydrocarbons, which comprises subjecting said fraction to extractive distillation in a first extractive distillation zone, separating a raffinate fraction comprising paraffins from an extract fraction comprising cycloparaffins of hydroaromatic and non-hydroaromatic structure in admixture with close boiling aromatic hydrocarbons in said first extractive distillation zone, passing said extract fraction from said first extractive distillation zone into a cycloparaffin fractionating zone, separating a vapor fraction comprising cycloparaffins of non-hydroaromatic structure and close boiling aromatic hydrocarbons from a liquid fraction consisting essentially of cycloparaffins of hydroaromatic structure free of any substantial amount of aromatic hydrocarbons in said cycloparaffin fractionating zone, passing said vapor fraction from said cycloparaffin fractionating zone into a second extractive distillation zone, separating a raffinate fraction comprising cycloparaffins of non-hydroaromatic structure free of any substantial amount of aromatic hydrocarbons from an extract fraction comprising aromatic hydrocarbons in said second extractive distillation zone with an isomerization catalyst at cycloparaffin isomerizing conditions in a conversion zone, thereby converting cycloparaffins of non-hydroaromatic structure to cycloparaffins of hydroaromatic structure in said conversion zone, passing effluence from said conversion zone into said cycloparaffin fractionating zone, and withdrawing said liquid fraction consisting essentially of cycloparaffins of hydroaromatic structure free of any substantial amount of aromatic hydrocarbons from said cycloparaffin fractionating zone.

7. The process for the production of cyclohexane free of any substantial amount of benzene from a hydrocarbon fraction comprising methylcyclopentane and cyclohexane in admixture with close boiling open chain paraffins and benzene which comprises subjecting said fraction to extractive distillation in a first extractive distillation zone, separating a raffinate fraction comprising paraffins and methylcyclopentane from an extract fraction comprising methylcyclopentane, cyclohexane and benzene in said first extractive distillation zone, passing said raffinate fraction from said first extractive distillation zone into a methylcyclopentane fractionating zone, separating a fraction comprising methylcyclopentane from a fraction comprising paraffins in said methylcyclopentane fractionating zone, passing said extract fraction from said first extractive distillation zone and said methylcyclopentane fraction from said methylcyclopentane fractionating zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone with an isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

8. The process for the production of cyclohexane free of any substantial amount of benzene from a hydrocarbon fraction comprising methylcyclopentane and cyclohexane in admixture with close boiling open chain paraffins and benzene which comprises subjecting said fraction to extractive distillation in a first extractive distillation zone, separating a raffinate fraction comprising paraffins and methylcyclopentane from an extract fraction comprising methylcyclopentane, cyclohexane and benzene in said first extractive distillation zone, passing said raffinate fraction from said first extractive distillation zone into a methylcyclopentane fractionating zone, separating a fraction comprising methylcyclopentane from a fraction comprising paraffins in said methylcyclopentane fractionating zone, passing said extract fraction from said first extractive distillation zone into a cycloparaffin fractionating zone, separating a vapor fraction comprising methylcyclopentane and benzene from a liquid fraction comprising cyclohexane free of any substantial amount of benzene in said cycloparaffin fractionating zone, passing said vapor fraction from said cycloparaffin fractionating zone into a second extractive distillation zone, separating a raffinate fraction comprising methylcyclopentane free of any substantial amount of benzene from an extract fraction comprising benzene in said second extractive distillation zone, contacting said raffinate from said second extractive distillation zone and said methylcyclopentane fraction from said methylcyclopentane fractionating zone with an isomerization catalyst at methylcyclopentane isomerizing conditions in a conversion zone, thereby converting methylcyclopentane to cyclohexane in said conversion zone, passing effluence from said conversion zone into said cycloparaffin fractionating zone, and withdrawing said liquid fraction consisting essentially of cyclohexane free of any substantial amount of benzene from said cycloparaffin fractionating zone.

RUSSELL N. SHIRAS.
ALAN C. NIXON.
CARL H. DEAL, JR.

No references cited.